United States Patent [19]

Sternberg et al.

[11] Patent Number: 4,510,811
[45] Date of Patent: Apr. 16, 1985

[54] METHOD FOR DISTINGUISHING BETWEEN INTERFERING SIGNALS AND SIGNALS INDICATING DEFECTS OF WORKPIECES DURING ULTRASONIC TESTING

[75] Inventors: Walter Sternberg, Alzenau; Fritz Schreyer, Langenselbold; Ursula Ruth, Ronneburg, all of Fed. Rep. of Germany

[73] Assignee: NUKEM GmbH, Hanau, Fed. Rep. of Germany

[21] Appl. No.: 455,554

[22] Filed: Jan. 4, 1983

[30] Foreign Application Priority Data

Feb. 11, 1982 [DE] Fed. Rep. of Germany ....... 3204797

[51] Int. Cl.³ .............................................. G01N 29/04
[52] U.S. Cl. ........................................ 73/611; 73/614; 73/615
[58] Field of Search .......................... 73/615, 611, 614

[56] References Cited

U.S. PATENT DOCUMENTS

| | | | |
|---|---|---|---|
| 3,608,363 | 9/1971 | Whittington | 73/615 |
| 3,690,156 | 9/1972 | Robinson | 73/615 |
| 3,929,006 | 12/1975 | Boggs | 73/609 |
| 4,147,065 | 4/1979 | Lather et al. | 73/611 |
| 4,150,577 | 4/1979 | Fetheroff | 73/611 |

Primary Examiner—Howard A. Birmiel
Attorney, Agent, or Firm—Cushman, Darby & Cushman

[57] ABSTRACT

In order to safely interfering signals caused by interfering volumina like e.g. air bubbles existing in a coupling medium from signals generated by workpiece defects in the ultrasonic testing of workpieces according to the pulse-echo-method, it is suggested that at the appearance of a signal in the time between transmitting pulse and surface echo-signal crossing an adjustable threshold during a test cycle, all signals of the same test cycle falling within the range of anticipation for workpiece defects will be suppressed.

2 Claims, 4 Drawing Figures

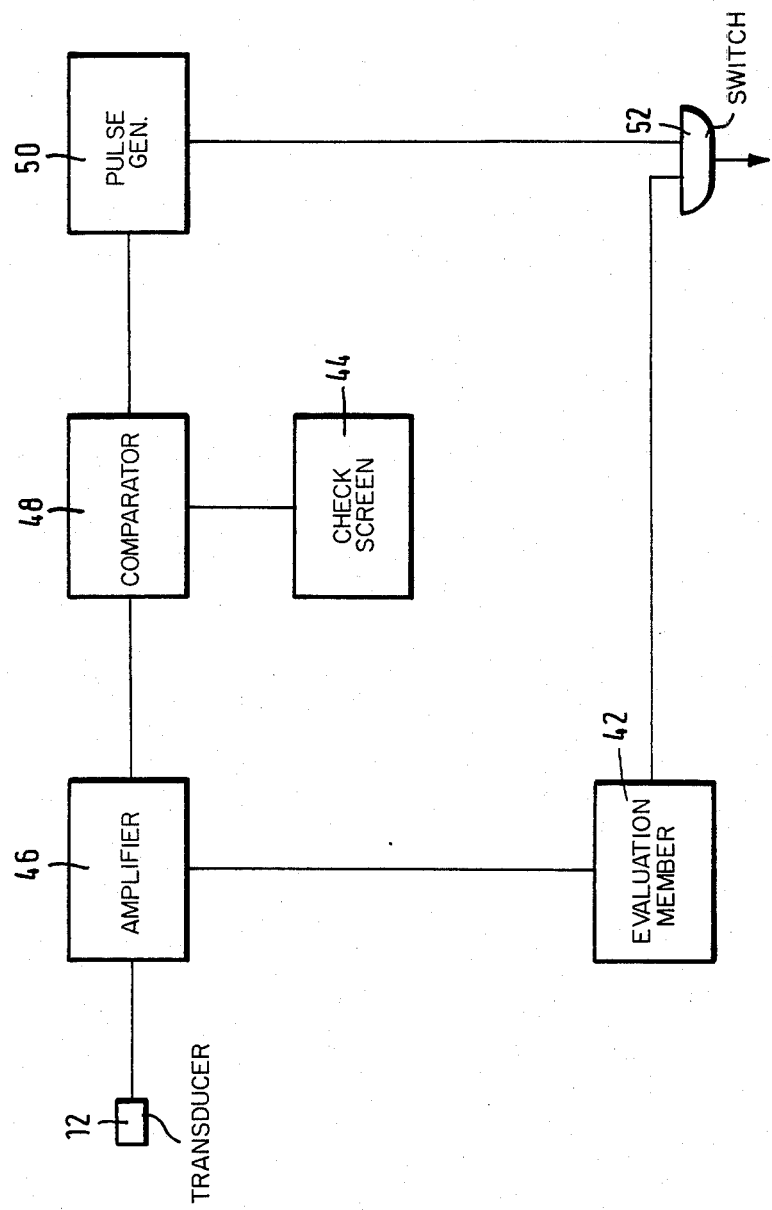

METHOD FOR DISTINGUISHING BETWEEN INTERFERING SIGNALS AND SIGNALS INDICATING DEFECTS OF WORKPIECES DURING ULTRASONIC TESTING

BACKGROUND OF THE INVENTION

The invention relates to a method for distinguishing between interfering signals caused e.g. by air bubbles, existing as interfering volumina in a coupling means and signals generated by workpiece defects during the ultrasonic testing of workpieces according to the pulse-echo-method.

The German Application No. 27 04 128 describes a method for a dynamic distinction between disturbance signals coming from small reflectors, like floating scales or air bubbles, and the true faults in the test piece at the ultrasonic test with a relative motion to the transducer and defects, where the transit times between transmitter pulse and subsequently received signals are compared in order to determine whether this is due to a flaw in the workpiece or to an interfering volume existing in the coupling means. For such a distinction it is required that the workpiece is to be turned relatively to the transducer in order to obtain a relative motion between the two, which is not existing to an interfering volume in the coupling means.

The German Disclosure 29 16 938 describes a method and an apparatus for reducing virtual signals by ultasonic testing in immersion technique. In order to eliminate interfering signals to a far extent, the ultrasonic transducer is surrounded by a snorkel made of a sound-absorbing material and preferably extending up to the surface of the test piece. Hereby it is guaranteed that any interfering volumina present at the outside of the snorkel region cannot influence the test results. However, if air bubbles or other particles are present within the snorkel region, the interfering signals can still be produced by them and lead to wrong elevations. If a snorkel end is directly adjacent at the workpiece, the workpiece cannot be set in rotation like it is very often required in the ultrasonic testing. A falsification of testing results can also happen if the sound waves oscillate between the ultrasonic transducer and an interfering reflector for several times so that multiple echoes are generated which are falling within the evaluation range of true faults and thus are simulating apparent defects. With the method described above, these multiple echoes cannot be eliminated and therefore represent considerable disadvantages of the known art.

SUMMARY OF THE INVENTION

It is the object of the present invention to provide a method of the kind as indicated in such a manner that the system is able to perform an exact scanning of interfering signals caused by multiple echoes in one test cycle separated from preceding or, respectively, susequent test cycles, and without using any mechanic expedients like e.g. screening elements.

According to the invention this object is obtained by producing a signal positioned between transmitting pulse and surface-echo of the workpiece and exceeding an adjustable threshold during a test cycle, any and all signals of the same test cycle falling within the expectation range of defects from the workpiece are suppressed. In other words, a pulse falling in the transit time of the ultrasonic signal in the water section—this between transmitting pulse and surface-echo—release a trigger signal so that the signals falling within the evaluation range for workpiece defects are not evaluated because otherwise pseudo-defects could be submitted to an evaluation. Consequently for each test cycle it can be found out without any mechanic expedients and with the known evaluation electronic whether the signals occuring in the evaluation range are generated by a real defect in the workpiece or by interfering reflectors present in the coupling means.

In self-invented embodiment of the invention it is suggested that the length of time t between transmitting pulse and interfering signal which appears before the surface echo of the workpiece is fixed, and that the signals falling within the range of anticipated defects of the workpiece n×t after the transmitting pulse are suppressed.

This suggested solution guarantees that only those signals falling in the evaluation range during a test cycle are suppressed which can be associated with a multiple echo of a disturber, so that pulses coming from a true defect which are falling in that region at the same time as the disturbing signal can still be evaluated further, thus resulting in an even better evaluation of workpieces in the non-destructive material testing.

The suggested solutions characterizing the invention, clearly show that in a simple manner there is offered a safe chance of detecting pulses caused by multiple echos falling within the evaluation region, so that the evaluation of the workpiece to be tested cannot be falsified by any interfering reflectors present in the coupling medium like e.g. air bubbles or floating scale.

Another advantage according to the invention is manifested in that the signals falling within the evaluation range must be subjected a evaluation of defects if no signal appears between transmitting pulse and surface echo or, respectively, does not cross the fixed threshold by adjusting the amplification; whereas, according to the prior art, each signal falling in the anticipation range must appear several times and in sequence in order to be definitely assigned to a defect. Therefore the invention facilitates a discrimination between true and false defects of workpieces.

BRIEF DESCRIPTION OF THE DRAWINGS

Further details, advantages and characteristics of the invention will be recognizable from the descriptions in the drawings where FIG. 4 is a block diagram.

DETAILED DESCRIPTION OF THE INVENTION

Figure 1:
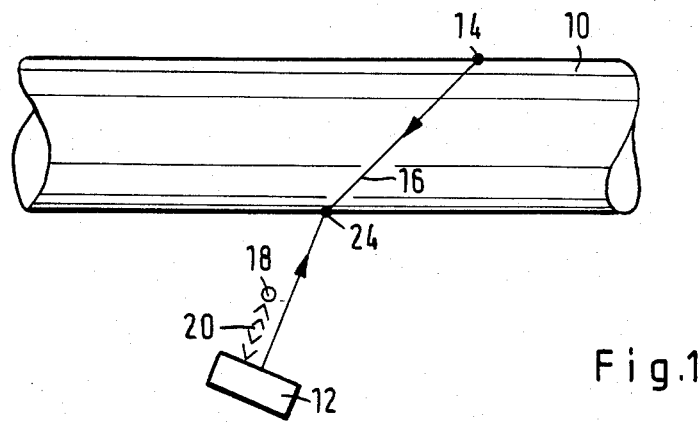
FIG. 1 shows a workpiece to be tested with diagrammatic view of the ultrasonic wave.

FIG. 1 shows a section of a workpiece 10 being exposed to ultrasonic waves by a transducer 12, where the coupling of the sound energy can take place e.g. via a water section. The workpiece 10 shall have a fault 14 which is detected by an ultrasonic wave 16. Further there shall be an interfering volume 18 in the coupling medium that is likewise being hit by a sound wave 20 which can run several times between the transducer 12 and the interfering volume 18.

Figure 2:
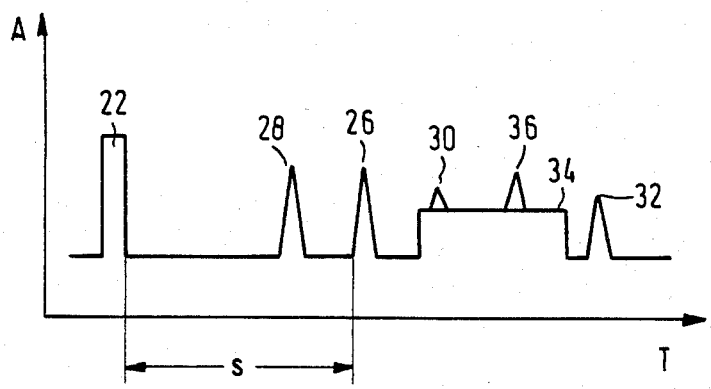
FIGS. 2 and 3 are ultrasonic images in amplitude/-time diagram.
Figure 3:
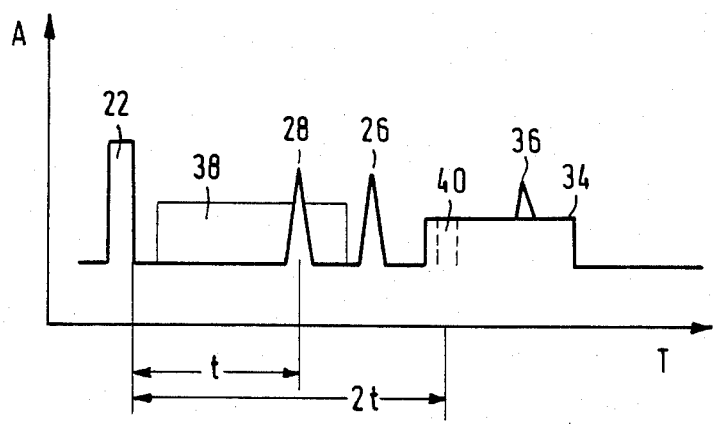

The excitation of ultrasonic sound wave is triggered by a transmitting pulse 22 diagrammatically shown in FIGS. 2 and 3. As soon as the ultrasonic waves hit the workpiece 10 (indicated with ref. 24), a part is reflected back to the transducer 12 so that an surface echo 26 will appear in the amplitude-time-diagram. The interval between the transmitting pulse 22 and the surface echo 26 is therefore representing the transit time s of the ultrasonics in the coupling medium.

A portion of the ultrasonic energy excited by the transmitter pulse 22 hits the interfering volume 18—indicated by the wave course 20—so that a reflection back to the ultrasonic transducer 12 takes place. The respective signal is indicated in the amplitude-time-diagram by reference 28. To the signal 28, relative to the transmitter pulse 22, further pulses 30, 32 can appear at the same distance resulting from the multiple reflections between the ultrasonic transducer and the interfering volume 18.

The pulses produced by true defects in the workpiece 10 are now falling in an evaluation range 34 as shown by pulse 36 which must be assigned to the defect 14. However, if now due to the interfering volume 18 multiple echoes and accompanying pulses 30 do appear, then in the evaluation range, in addition to the one true defect 14 characterized by pulse 36, one can defect a further pulse 30 which incorrectly can likewise be evaluated as a true fault in the workpiece.

In order to avoid this, according to the invention a monitoring of signals takes place that are crossing an adjustable threshold 38 during the transit time s. Thereby the time period wherein the monitoring takes place is between the surface echo and that of the inclined right flank of the transmitting pulse 22, thus being shorter/equal or s. Like it is shown in FIG. 3, the pulse 28 generated by the interfering volume 18 is crossing the threshold 38. For the evaluation electronics this means that all signals falling within the evaluation range 34 in this test cycle are not processed any further in order to exclude the evaluation of apparent sound errors.

As an alternative to the foregoing, the time of appearance t of the interfering pulse 28 after the transmitting pulse 22 can be determined and recorded in order to make ineffective only that portion of the evaluation range 34 corresponding to a multiple of the time t. This means that the region 40 of the evaluation range 34 according to FIG. 3 is left out of account at the evaluation, thus signals falling in this region 40 will not be further processed since this region as far as time is concerned it is positioned in the area after the transmitting pulse 22. On the other hand, the signal 36 produced by the interfering point 14 can be fed to the customary electronic further processing.

The block diagram presented in FIG. 4 shows an elevation electronic by means of which the processing of the ture trouble signals and the suppression of false signals is rendered possible.

The signals coming from the transducer 12, via an amplifier 46 are led to a comparator 48 and an evaluation member 42, which presets the screen and threshold for the evaluation range 34. As soon as the signals at the comparator 48 are crossing the adjustable threshold 38 and fall within the check screen 44 (corresponds to time interval during the transit time s in the coupling medium), the comparator will be actuated. Thereby a switch 52 is closed at which there are likewise standing signals coming from the evaluation member 42 so that these will not be evaluated for the pending test cycle as they could be false defect signals. Via a pulse generator 50 the signals coming the comparator 48 can be cancelled in order to be able to re-evaluated the signals occuring in the subsequent test cycle.

We claim:
1. A process for the ultrasonic, non-destructive testing of a workpiece disposed in a liquid medium where a transducing means is employed to expose the workpiece to acoustic waves traveling through the liquid medium and an interference member is disposed in the liquid medium between the workpiece and the transducer, comprising the steps of:
   transmitting a first impulse wave from the transducing means,
   detecting the first echo of said first impulse wave from the surface of the workpiece and noting the elapsed time period between the transmission and detection of the echo of said first impulse wave, said elapsed time period defining a time zone and corresponding to an area of wave transmission wherein unwanted obstructions could be located resulting in an unwanted echo signal,
   establishing with said interference member an adjustable threshold signal level, and
   suppressing, during a test cycle, any signal which exceeds said threshold signal level and which falls within said time zone.
2. The process as claimed in claim 1, further including the step of determining a time period defined by the time elapsed for a signal originating from the transducer and the detection of the echo of said signal from the surface of the work piece and suppressing detection of all signals falling within n multiplied by said time period where n is an integer greater than one.

* * * * *